United States Patent
Anbar et al.

(10) Patent No.: US 9,261,519 B2
(45) Date of Patent: Feb. 16, 2016

(54) ISOTOPIC BIOMARKERS FOR RAPID ASSESSMENT OF BONE MINERAL BALANCE IN BIOMEDICAL APPLICATIONS

(75) Inventors: Ariel Anbar, Tempe, AZ (US); Joseph Skulan, Lodi, WI (US); Gwyneth Gordon, Tempe, AZ (US); Jennifer Morgan, Houston, TX (US)

(73) Assignee: Arizona Board of Regents, a Body Corporate of the State of Arizona Acting for and on Behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 13/703,103

(22) PCT Filed: Jun. 9, 2011

(86) PCT No.: PCT/US2011/039780
§ 371 (c)(1),
(2), (4) Date: Jan. 18, 2013

(87) PCT Pub. No.: WO2011/156583
PCT Pub. Date: Dec. 15, 2011

(65) Prior Publication Data
US 2013/0115650 A1 May 9, 2013

Related U.S. Application Data

(60) Provisional application No. 61/353,267, filed on Jun. 10, 2010.

(51) Int. Cl.
*G01N 33/84* (2006.01)
*G01N 33/50* (2006.01)

(52) U.S. Cl.
CPC ............ *G01N 33/84* (2013.01); *G01N 33/5005* (2013.01); *G01N 2458/15* (2013.01)

(58) Field of Classification Search
None
See application file for complete search history.

(56) References Cited

U.S. PATENT DOCUMENTS

| 5,912,178 | A | 6/1999 | Porter et al. |
| 6,764,817 | B1 | 7/2004 | Schneider |
| 7,078,059 | B2 | 7/2006 | Atherton et al. |
| 2006/0115427 | A1 | 6/2006 | Hillegonds et al. |

FOREIGN PATENT DOCUMENTS

WO 2007106149 A2 9/2007

OTHER PUBLICATIONS

Skulan, Joseph; et al; "Natural Calcium Isotopic Composition of Urine as a Marker of Bone Mineral Balance" Clinical Chemistry, 53, 1155-1158, 2007.*
Abrams, Steven A; et al; "Relationships among Vitamin D Levels, Parathyroid Hormone, and Calcium Absorption in Young Adolescents" The Journal of Clinical Endocrinology & Metabolism, 90, 5576-5581, 2005.*
Hillman, Laura S; et al; "Percent True Calcium Absorption, Mineral Metabolism, and Bone Mass in Children With Arthritis" Arthritis & Rheumatism, 58, 3255-3263, 2008.*
Heuser, Alexander; Eisenhauer, Anton; "A pilot study on the use of natural calcium isotope (44Ca/40Ca) fractionation in urine as a proxy for the human body calcium balance" Bone, 46, 889-896, 2010.*
Dahl, SG; et al; "Incorporation and Distribution of Strontium in Bone" Bone, 28, 446-453, 2001.*
Abrams, SA; O'Brien, KO; "Calcium and Bone Mineral Metabolism in Children with Chronic Illnesses" Annual Review of Nutrition, 24, 13-32, 2004.*
Skulan, Joseph, et al., "Calcium isotope fractionation between soft and mineralized tissues as a monitor of calcium use in vertebrates," Proc. Natl. Acad. Sci. U.S.A., Nov. 1999, pp. 13709-13713, vol. 96, No. 24.
Skulan, Joseph, et al., "Natural calcium isotopic composition of urine as a marker of bone mineral balance," Clin. Chem., Jun. 2007, pp. 1155-1158, vol. 53, No. 6.
Krayenbuehl, Pierre-Alexandre, et al., "Hereditary hemochromatosis is reflected in the iron isotope composition of Blood," Blood, May 2005, pp. 3812-3816, vol. 105, No. 10.
Walczyk, Thomas, "Natural Iron Isotope Variations in Human Blood," Science, Mar. 2002, pp. 2065-2066, vol. 295, No. 5562.
Riggs, B. Lawrence, "Overview of Osteoporosis," West J. Med., Jan. 1991, pp. 63-77, vol. 154.
Hirata, Takafumi, et al., "Isotopic analysis of calcium in blood plasma and bone from mouse samples by multiple collector-ICP-mass spectrometry," Anal. Sci., Nov. 2008, pp. 1501-1507, vol. 24, No. 11.
Price, T.D., et al., "The characterization of Biologically Available Strontium Isotope Ratios for the Study of Prehistoric Migration," Arachaeometry, Feb. 2002, pp. 117-135, vol. 44, No. 1.
Wieser, Michael E., et al., "High precision calcium isotope ratio measurements using a magnetic sector multiple collector inductively coupled plasma mass spectrometer," J. Anal. At. Spectrum, 2004, pp. 884-851, vol. 19.
International Search Report and Written Opinion for PCT/US2011/039780.
International Preliminary Report on Patentability for PCT/US2011/039780.

* cited by examiner

*Primary Examiner* — Renee Claytor
*Assistant Examiner* — David Berke-Schlessel
(74) *Attorney, Agent, or Firm* — Quarles & Brady LLP; Gavin J. Milczarek-Desai (57) ABSTRACT

The present invention relates to the use of natural isotopes $^{44}Ca/^{42}Ca$ $^{87}Sr/^{86}Sr$ as biomarkers to measure changes in bone mineral balance and loss.

15 Claims, 5 Drawing Sheets

ISOTOPIC BIOMARKERS FOR RAPID ASSESSMENT OF BONE MINERAL BALANCE IN BIOMEDICAL APPLICATIONS

This application is a 371 application of PCT/US2011/039780 filed Jun. 9, 2011 which claims priority based on U.S. Provisional Application No. 61/353,267, which was filed Jun. 10, 2010. The entire text of the aforementioned applications are incorporated herein by reference.

FIELD OF THE INVENTION

Background of the Invention

It is well recognized that the bone mass of an individual changes throughout life and that there are certainly a number of distinct phases of changes that occur (see Riggs, West J. Med. 154:63-77, 1991). The first phase, during which a peak in bone mass is attained, occurs in both men and women and is typically characterized by a linear growth of the endochondral growth plates, and radial growth due to a rate of periosteal apposition. The second phase begins around age 30 for trabecular bone and about age 40 for cortical bone and continues to old age is characterized by slow bone loss, and occurs in both men and women. In women, there is a third phase of bone loss that occurs likely as a result of a drop in estrogen following menopause. During this phase, women may lose an additional 10% of bone mass from the cortical bone and 25% from the trabecular compartment.

Loss of bone mineral content leads to a variety of significant medical problems. Most notably, osteoporosis is a debilitating disease characterized by marked decreases in skeletal bone mass and mineral density, structural deterioration of bone including degradation of bone microarchitecture and corresponding increases in bone fragility and susceptibility to fracture in afflicted individuals. Osteoporosis in humans is preceded by clinical osteopenia (defined as bone mineral density that is below the mean value for young adult bone by greater than one standard deviation but less than 2.5 standard deviations)). Osteopenia is a condition found in approximately 25 million people in the United States. Another 7-8 million patients in the United States have been diagnosed with clinical osteoporosis (defined as bone mineral content below that of mature young adult bone by greater than 2.5 standard deviations). Osteoporosis is one of the most expensive diseases for the health care system, costing tens of billions of dollars annually in the United States. In addition to health care-related costs, long-term residential care and lost working days add to the financial and social costs of this disease. Worldwide approximately 75 million people are at risk for osteoporosis.

Incidence of osteoporosis increases with age, and among Caucasians is predominant in women; Caucasian women comprise 80% of the osteoporosis patient pool in the United States. Osteoporosis can lead, for example, to vertebral and/or non-vertebral fractures. Vertebral fractures are those involving the spinal column and non-vertebral fractures refers to any fracture not involving the spinal column. Non-vertebral fractures are more common than fractures of the vertebrae—an estimated 850,000 non-vertebral compared with 700,000 vertebral fractures occur annually in the United States. Non-vertebral fractures include more than 300,000 hip and 250,000 wrist fractures, in addition to 300,000 fractures at other non-vertebral sites. Other examples of non-vertebral fractures include a fracture of a distal forearm, a fracture of a proximal humerus, a fracture of a wrist, a fracture of a radius, a fracture of an ankle, a fracture of an humerus, a fracture of a rib, a fracture of a foot, a fracture of a pelvis, or any combination of these fractures. Fractured hips, wrists, and vertebrae are among the most common injuries associated with osteoporosis. Hip fractures in particular are extremely uncomfortable and expensive for the patient, and for women correlate with high rates of mortality and morbidity. Although osteoporosis has been defined as an increase in the risk of fracture due to decreased bone mass, none of the presently available treatments for skeletal disorders can substantially increase the bone density of adults.

At its most basic level, osteoporosis can be characterized as an Imbalance between bone formation and resorption. As such, measuring the balance of bone formation and resorption is central to effective diagnosis and therapeutic intervention of osteoporosis. At present, net bone mineral balance is assessed by measuring bone mineral density—i.e., once bone damage has already occurred. There is a widely recognized need for clinically useful techniques to measure net bone mineral balance prior to the onset of clinically detectable bone damage and to monitor the course of treatment. However, no such techniques exist at this time.

Biochemical markers indicative of bone formation or loss exist. However, they suffer from imprecision, inability to provide quantitative estimates of bone formation and resorption mechanisms and do not provide useful information on the critical variable: net bone mineral balance. These markers are not clinically useful. Thus, there is a need for biomarkers that can be used for the assessment and diagnosis of bone mineral imbalance.

BRIEF SUMMARY OF THE INVENTION

The present invention provides methods and compositions relating to the use of natural isotope biomarker techniques to assess and diagnose bone mineral imbalance. These techniques could be employed in both research and clinical settings for the early detection of bone mineral imbalance leading to bone disease and for rapidly assessing the effectiveness of treatments aimed at altering bone mineral balance.

The use of natural isotopes ($^{44}Ca/^{42}Ca$ or $^{87}Sr/^{86}Sr$) as biomarkers can measure changes in bone mineral balance and loss. An isotopic baseline is first established in the patient using a dietary regime or $^{44}Ca/^{42}Ca$ bolus administration (in the case of calcium) or feeding of naturally-derived $^{87}Sr/^{86}Sr$ (in the case of strontium). The net bone mineral balance is determined by analyzing changes in the natural isotope composition in various patient samples resulting from the balance of bone formation vs. resorption. In the case of calcium, common dietary sources can have differences in $^{44}Ca/^{42}Ca$ large enough to swamp the effect of bone mineral balance. This new method uses several techniques to overcome this limitation, including evaluation of a patient's normal dietary habits to establish source of $^{44}Ca/^{42}Ca$ variations, mild dietary restrictions if necessary, and the use of short-term data (blood, urine) and long-term data (hair sample analysis). In the case of strontium, a natural isotope tracer, $^{87}Sr/^{86}Sr$, is used to create and sustain an isotopic offset between dietary strontium and strontium originating in bone. This technique can be used to measure the rate of bone mineral loss or resorption.

Sample analysis is performed using multiple collector inductively coupled plasma mass spectrometry (MC-ICP-MS) using newly developed sampling techniques for $^{44}Ca/^{42}Ca$ and $^{87}Sr/^{86}Sr$. This new diagnostic technique has a number of potential advantages including the ability to measure bone mineral balance directly, earlier detection (isotopes respond to changes in bone mineral balance approximately two orders of magnitude faster than bone mineral density detectable by x-ray densitometry), and does not require the administration of synthetic radioactive tracers.

DETAILED DESCRIPTION OF THE INVENTION

The development of new treatments for metabolic bone disease, and evaluation of the effectiveness of existing therapies in individual patients are severely hampered by the lack of any reliable tool for quickly measuring changes in bone mineral balance in response to treatment. In the present invention two new methods are identified that can either be used individually or simultaneously to reliably measure changes in bone mineral balance in response to any given intervention or over time. In the first embodiment, a new tracerless calcium isotope biomarker of bone mineral balance is used. When properly applied, the calcium isotope biomarker reveals changes in bone mineral balance with unprecedented speed and detail, and has the potential to dramatically improve the treatment for diseases such as osteoporosis. A complimentary strontium isotope biomarker provides, with equal rapidity, information on the speed of exchange of calcium between soft tissue and mineralized compartments.

The present invention relates to two separate groups of isotopes that can be used as biomarkers for rapidly and efficiently assessing bone mineral imbalance. The first embodiment relates to a tracer-less calcium isotope technique that measures net bone mineral balance by analyzing changes in the natural calcium isotope composition in blood and urine resulting from the balance of bone formation versus bone resorption. This is the only technique that is able to measure net bone mineral balance before the onset of bone loss.

In a second embodiment, the present invention relates to a strontium isotope tracer technique that exploits natural variations in $^{87}Sr/^{86}Sr$ to create and sustain an isotopic offset between dietary strontium and strontium originating in bone, which can be used to measure the rate of bone mineral loss. This technique differs from standard isotope tracer techniques, which give no direct information on bone mineral loss and which require administration of an artificially purified isotope.

The monitoring techniques using the calcium isotopes can be combined with those that use the strontium isotope tracer to produce a powerful technique for measuring changes in bone mineral balance.

The Calcium Method

Natural calcium is a mixture of six isotopes (masses 40, 42, 43, 44, 46, and 48). The relative abundances of these isotopes are altered when calcium minerals, including bone mineral (calcium phosphate), are precipitated from aqueous solution. This alteration in isotope composition, or 'fractionation,' results in calcium minerals being enriched in the lighter (lower mass) calcium isotopes relative to the solution from which they precipitated, while the solution becomes enriched in isotopically heavy calcium. The dissolution of calcium minerals, on the other hand, does not significantly fractionate calcium isotopes. This asymmetry between the isotopic effects of bone mineral formation and dissolution causes systematic and measureable changes in the calcium isotope composition of blood and urine, such that when bone mineral balance shifts so that bone formation exceeds bone dissolution (positive bone mineral balance) the Ca isotope composition of blood and urine become heavier, while when bone dissolution exceeds bone formation the isotope composition of blood and urine becomes lighter. Changes in Ca isotope composition are expressed as the ratio of any two calcium isotopes, with the heavier isotope in the numerator. The most commonly reported ratios are $^{44}Ca/^{40}Ca$ and $^{44}Ca/^{42}Ca$. in both cases a rise in the value of the ratio indicates that calcium has become enriched in the heavier isotope, and a decrease that calcium has become less.enriched in the lower mass isotope. When Ca isotopes are measured by multi-collector inductively coupled plasma mass spectrometry the ratio of $^{44}Ca/^{42}Ca$ typically is used, in order to avoid interference from $^{40}Ar$. Calcium isotope composition hereafter is referred to as $^{44}Ca/^{42}Ca$.

Thus the present invention recognizes that the $^{44}Ca/^{42}Ca$ of soft tissues, and of materials like saliva, urine and hair that are derived from soft tissues, are strongly affected by bone mineral balance. Measurements in these materials will provide information about bone mineral balance.

Calcium isotopes in urine vary in accordance with the expectations above over a timescale of many weeks. However, the present invention for the first time is able to achieve a clinical application of these calcium isotopes to produce high throughput data over a time scale of a few hours or days or monitoring. The ability of the technique to rapidly detect changes in bone mineral balance minimizes the effect of variation created by dietary the $^{44}Ca/^{42}Ca$. Common dietary sources of calcium can have differences in $^{44}Ca/^{42}Ca$ large enough to swamp the effect of bone mineral balance. Control of this dietary calcium composition over a period of many weeks is difficult to imagine outside of research settings.

The present inventors have shown that the calcium isotope composition of urine varies rapidly, on a timescale of days, or even hours, rather than weeks as previously reported. This rapid response both increases the potential usefulness of the calcium isotope biomarker, and raises additional technical issues that must be addressed before it can find clinical use.

Variation in the $^{44}Ca/^{42}Ca$ of diet must be accounted for. Common dietary sources of calcium can have differences in $^{44}Ca/^{42}Ca$ large enough to swamp the effect of bone mineral balance. In order to combat this problem, the patient's normal dietary habits are monitored to determine whether variations in dietary $^{44}Ca/^{42}Ca$ are large enough to induce significant imprecision in the bone mineral balance calculation. If so, the problem can be addressed by imposing mild dietary restrictions or supplementation.

In addition, the present invention takes into account the effects of short term fluctuations in bone mineral balance and distinguishes them from long term trends that control changes in skeletal mass large enough to be clinically significant. This is done by analyzing a series of urine or blood samples collected over a period of days, collected at the same time each day. Alternatively, or in combination with analysis of the blood and urine samples, analysis of hair samples also is performed as this analysis reflects longer-term soft tissue $^{44}Ca/^{42}Ca$ than blood or urine.

A further alternative for dealing with sources of calcium isotope noise in the bone mineral signal in $^{44}Ca/^{42}Ca$ is to intentionally perturb $^{44}Ca/^{42}Ca$ or to deliberately perturb bone mineral balance in a known way. One way to employ perturbation of $^{44}Ca/^{42}Ca$ would be to replace as much dietary calcium as possible with a calcium supplement of known $^{44}Ca/^{42}Ca$ for a period of time before sampling and during sampling. The $^{44}Ca/^{42}Ca$ of this supplement would be adjusted to match, as closely as possible, the average $^{44}Ca/^{42}Ca$ of the patient's normal diet. The effect of these supplements would be to smooth out normal fluctuations in dietary $^{44}Ca/^{42}Ca$. The supplements could be manufactured and customized by mixing calcium from various natural sources, ranging from seawater as a source for very high $^{44}Ca/^{42}Ca$ to the bones of large mammalian predators for very low $^{44}Ca/^{42}Ca$. The use and manufacture of these supplements (like the strontium supplements discussed below) is part of the invention disclosed here.

Perturbation also could take the form of a large bolus of calcium with an unusual $^{44}Ca/^{42}Ca$ (compared to the normal dietary value of each patient). Change in soft tissue $^{44}Ca/^{42}Ca$ following administration of the bolus would be closely monitored for several days, and intermittently monitored until the perturbation no longer could be detected (up to a few months for a large perturbation). The information revealed by this type of perturbation would be fundamentally different from what the other techniques describe here would show, because in addition to giving information about bone mineral balance it also would permit the calculation of residence time of calcium in soft tissues, and could constrain rates of calcium uptake by the skeleton, particularly if urinary calcium excretion were measured simultaneously. We have done no experiments with this kind of perturbation, but the theoretical basis for developing a perturbation technique are partially developed in literature on stable calcium isotope tracer kinetics.

A different type of perturbation study would involve comparing $^{44}Ca/^{42}Ca$ in blood or urine samples before and after normal nocturnal bed rest. This idea relies on the rapid response of $^{44}Ca/^{42}Ca$ to changes in bone loading. It seems likely that the short-term change in $^{44}Ca/^{42}Ca$ in response to bed rest differs among patients in a way that relates to their general bone mineral balance.

Regardless of the particular method used, the simplest approach is to use calcium isotopes not to measure absolute bone mineral balance, but instead to measure changes in bone mineral balance over time, taking advantage of the rapid response of this marker that we have discovered in research to date. A baseline soft tissue $^{44}Ca/^{42}Ca$ would be taken for each patient; future changes in bone mineral balance would be reflected as deviations from this baseline. Such an approach would be suitable for long-term monitoring of bone mineral balance, but also for monitoring short-term changes in response to treatment. Being able to quickly judge the effectiveness of treatments intended to increase bone mass is the single greatest advantage of $^{44}Ca/^{42}Ca$, as such evaluation is impossible with other biomarkers or with densitometry techniques like DEX.

Calcium isotopic compositions are expressed as $\delta^{44}Ca$, or the difference in parts per thousand between the $^{44}Ca/^{42}Ca$ of a sample and the $^{44}Ca/^{42}Ca$ of a standard reference material. $\delta^{44}Ca$ was measured in urine samples from 10 persons who participated in a study of the effectiveness of countermeasures to bone loss in spaceflight, in which 17 weeks of bed rest was used to induce bone loss. Study participants were assigned to 1 of 3 treatment groups: controls received no treatment, one treatment group received alendronate, and another group performed resistive exercise. Measurements were made on urine samples collected before, at 2 or 3 points during, and after bed rest. (see Skulan et al. Clinical Chemistry 53, No. 6, 2007). Similar methods can be used therein can be used to calculate the $^{44}Ca/^{42}Ca$ ratio in the urine of subjects in the present methods.

The Strontium Method

Strontium is naturally present in the human diet, where it occurs as a minor contaminant of calcium. Strontium is chemically similar to calcium and follows calcium throughout the body, and so can be used as a calcium tracer. The ratio of two naturally occurring stable isotopes of strontium, $^{87}Sr/^{86}Sr$, varies between different dietary sources. $^{87}Sr/^{86}Sr$ of urine is determined by the $^{87}Sr/^{86}Sr$ of diet and of strontium already present in the body. The bulk of strontium in the body is in bone, and the $^{87}Sr/^{86}Sr$ of bone reflects the long-term dietary average. By altering dietary $^{87}Sr/^{86}Sr$ to a value different from that of the long-term dietary average and holding it at that value for a period of days, it is possible to use measurement of urinary $^{87}Sr/^{86}Sr$ to accurately determine the rate of bone resorption, something that cannot be done with current clinical techniques. Studies performed in rhesus monkeys shows that this method does reveal changes in bone mineral balance. Alternatively, the $^{87}Sr/^{86}Sr$ of bone itself may be altered by administering doses of Sr with an unusually high $^{87}Sr/^{86}Sr$ for a period of weeks and then ceasing the doses for a period of 1-2 weeks, after which time the skeleton will be the only reaming source of high $^{87}Sr/^{86}Sr$.

The use of a Sr tracer technique is fundamentally different from most other tracer techniques in that it creates an isotopic offset between diet and skeletal mineral, effectively giving the skeleton a distinctive isotopic signature. In a significant advantage, the Sr technique does not use radioisotopes and does not require accelerator mass spectrometry.

Sr with high $^{87}Sr/^{86}Sr$ can be extracted from ancient bedrock. In the United States the largest source of rock is the Lake Superior region. Extraction of isotopically distinct Sr from ancient rocks, and the incorporation of this Sr into orally administered doses of precisely known $^{87}Sr/^{86}Sr$ is part of the invention disclosed herein.

The calcium and strontium isotope techniques give similar but not identical information. $^{44}Ca/^{42}Ca$ provides direct information about net bone mineral balance than $^{87}Sr/^{86}Sr$, while strontium isotopes gives direct information about bone resorption. Both techniques reveal details of the speed of exchange of calcium between various soft tissue and mineralized compartments. The two techniques can be used simultaneously.

A chief advantage of the strontium technique is that it could be put to clinical use almost immediately. This is because $^{87}Sr/^{86}Sr$ of blood and urine are determined solely by the mixing of isotopically distinct "old" strontium, which after about ten days is derived almost entirely from bone, and "new" dietary strontium. As it is physically impossible for any biological process other than such mixing to affect $^{87}Sr/^{86}Sr$, interpreting strontium isotopic data in terms of bone mineral balance is simple.

Both the use of $^{44}Ca/^{42}Ca$ and $^{87}Sr/^{86}Sr$ in the diagnostic and assessment methods of the present invention require a high-throughput method to analyze isotope compositions of the elements involved. High-throughput is required because the changes being monitored happen rapidly, and because eventual clinical application would only be economical with such a method.

Previously, analyses of Ca and Sr isotopes have been done primarily using thermal ionization mass spectrometry (TIMS). TIMS analyses are slow, labor-intensive and cannot easily be automated. In the present invention, the monitoring is instead achieved using multiple collector inductively coupled plasma mass spectrometry (MC-ICP-MS). This method intrinsically allows 5-10 times higher sample throughput than TIMS. It also offers the potential for an automated process for Ca and Sr isotope analyses. A key stumbling block to the use of MC-ICP-MS for such analyses on biological samples are interferences arising from chemical impurities in the samples. These must be eliminated by chemical preparation methods. These problems are not recognized in the published literature, which focuses on geological rather than biological samples. We have identified and resolved these issues for the measurement of $^{44}Ca/^{42}Ca$ and $^{87}Sr/^{86}Sr$. We have also begun to consider the possibility that advanced spectrophotometric methods could be used for rapid Ca isotope measurements. This has never been done to the required precision but may be feasible.

Bone Disorders

The methods of the present invention can be used to determine the bone mineral imbalance for any bone deficit disorder or to determine the efficacy of treatment of a bone deficit disorder. In order for a treatment to be effective in treating a bone deficit disorder, it is desirable that the treatment results in an increase in the level of bone formation and/or a decrease in the level of bone resorption such that there is an overall increase in bone mass or density. It should be understood therefore that a subject having a bone deficit disorder is one who has less bone than desirable or that the bone will be less dense or strong than desired. A bone deficit may be localized, such as that caused by a bone fracture, or systemic, such as that caused by osteoporosis. Bone deficits may result from a bone remodeling disorder whereby the balance between bone formation and bone resorption is shifted, resulting in a bone deficit. Examples of such bone remodeling disorders include, for example, osteoporosis, Paget's disease, renal osteodystrophy, renal rickets, osteoarthritis, rheumatoid arthritis, achondroplasia, osteochodrytis, hyperparathyroidism, osteogenesis imperfecta, congenital hypophosphatasia, fribromatous lesions, fibrous displasia, multiple myeloma, abnormal bone turnover, osteolytic bone disease and periodontal disease. Bone remodeling disorders includes metabolic bone diseases which are characterized by disturbances in the organic matrix, bone mineralization, bone remodeling, endocrine, nutritional and other factors which regulate skeletal and mineral homeostasis. Such disorders may be hereditary or acquired and generally are systemic, affecting the entire skeletal system.

Thus, in one aspect the human subject may have a bone remodeling disorder. Bone remodeling as used herein refers to the process whereby old bone is being removed and new bone is being formed by a continuous turnover of bone matrix and mineral that involves bone resorption by osteoclasts and bone formation by osteoblasts. Osteoporosis is a common bone remodeling disorder characterized by a decrease in bone density of normally mineralized bone, resulting in thinning and increased porosity of bone cortices and trabeculae. The skeletal fragility caused by osteoporosis predisposes sufferers to bone pain and an increased incidence of fractures. Progressive bone loss in this condition may result in a loss of up to 50% of the initial skeletal mass. Primary osteoporosis includes idiopathic osteoporosis which occurs in children or young adults with normal gonadal function, Type I osteoporosis, also described as post-menopausal osteoporosis, and Type II osteoporosis, senile osteoporosis, occurs mainly in those persons older than 70 years of age. Causes of secondary osteoporosis may be endocrine (e.g., glucocorticoid excess, hyperparathyroidism, hypoganodism), drug induced (e.g. corticosteroid, heparin, tobacco) and miscellaneous (e.g., chronic renal failure, hepatic disease and malabsorbtion syndrome osteoporosis).

The phrase "at risk of developing a bone deficit", as used herein, is intended to embrace subjects having a higher than average predisposition towards developing a bone deficit. As an example, those susceptible towards osteoporosis include post-menopausal women, elderly males (e.g., those over the age of 65) and those being treated with drugs known to cause osteoporosis as a side-effect (e.g., steroid-induced osteoporosis). Certain factors are well known in the art which may be used to identify those at risk of developing a bone deficit due to bone remodelling disorders like osteoporosis. Risk factors for osteoporosis are known in the art and include hypogonadal conditions in men and women, irrespective of age, conditions, diseases or drugs that induce hypogonadism, nutritional factors associated with osteoporosis (low calcium or vitamin D being the most common), smoking, alcohol, drugs associated with bone loss (such as glucocorticoids, thyroxine, heparin, lithium, anticonvulsants etc.), loss of eyesight that predisposes to falls, conditions of microgravity encountered in space travel, immobilization, chronic hospitalization or bed rest, and other systemic diseases that have been linked to increased risk of osteoporosis. The present invention is one that allows the diagnosis of an increased risk in the development of a bone deficit simply by monitoring the calcium and strontium isotope levels as described herein.

The methods of the invention will also be useful for monitoring the efficacy of therapy to a subject that may suffer or have suffered trauma to one or more bones. The method can benefit mammalian subjects, such as humans, horses, dogs, and cats, in particular, humans. Bone trauma can be a problem for racing horses and dogs, and also for household pets. A human can suffer any of a variety of bone traumas due, for example, to accident, medical intervention, disease, or disorder. In the young, bone trauma is likely due to fracture, medical intervention to repair a fracture, or the repair of joints or connective tissue damaged, for example, through athletics. Other types of bone trauma, such as those from osteoporosis, degenerative bone disease (such as arthritis or osteoarthritis), hip replacement, or secondary conditions associated with therapy for other systemic conditions (e.g., glucocorticoid osteoporosis, burns or organ transplantation) are found most often in older people.

The methods of the invention can be used to determine whether the subject is at risk of having such fractures as determined by an overall increase in the lighter isotopes of the calcium or strontium in the blood, urine or hair samples of the subject over time. In addition, the methods of the invention will be useful in assessing the effectiveness of a given therapy in increasing the bone density of the subject in that an increase in the heavier isotopes of the calcium and strontium in the blood urine or hair samples of the subject in response to the therapy will be indicative of an increase in bone formation and/or a decrease in bone resoption in response to the therapy.

In specific embodiments, a preferred subject is a postmenopausal woman. The methods of the present invention may be particularly useful in early stage detection of osteoporosis.

Other subjects can also be at risk of or suffer bone trauma and can benefit from the diagnostic methods of the invention. For example, a wide variety of subjects at risk of one or more of the fractures identified above, can anticipate surgery resulting in bone trauma, or may undergo an orthopedic procedure that manipulates a bone at a skeletal site of abnormally low bone mass or poor bone structure, or deficient in mineral. For example, recovery of function after a surgery such as a joint replacement (e.g. knee or hip) or spine bracing, or other procedures that immobilize a bone or skeleton can improve due to the method of the invention. The method of the invention can be used to monitor the level of bone strength in such subjects prior to any of these procedures and also be used to monitor the efficacy of the treatment throughout the procedure and as a post-operative monitoring to ensure that the therapeutic intervention is effective. The methods will also aid recovery from orthopedic procedures that manipulate a bone at a site of abnormally low bone mass or poor bone structure, which procedures include surgical division of bone, including osteotomies, joint replacement where loss of bone structure requires restructuring with acetabulum shelf creation and prevention of prosthesis drift, for example. Other suitable subjects for practice of the present invention include those suffering from hypoparathyroidism or kyphosis, who can undergo trauma related to, or caused by, hypoparathyroidism or progression of kyphosis. Each of these subjects may be given additional therapeutic agents and the effect of those therapeutic agents can be continuously monitored using the isotope-based monitoring methods described herein.

A specific group of therapeutic agents that can be monitored using the methods of the present invention are parathyroid hormone and analogues thereof, including the native PTH as well as its truncated 1-34 form. These agents are well known in the art and are effective to induce bone formation and inhibit or reduce bone loss or resorption. Numerous such analogues are known. The methods of the present invention can be used to determine the efficacy of the various analogues as well as to optimize and select pharmaceutically acceptable doses thereof. For example, the methods of the present invention can be used to determine the effectiveness of a method for treating osteoporosis by administering to a subject in need thereof a pharmaceutically acceptable formulation comprising a PTH peptide analogue in a daily dose of 2 µg to 60 µg or a weekly dose of from 14 µg to 420 µg, and concomitantly monitoring the presence of $^{44}Ca/^{42}Ca$ and/or $^{87}Sr/^{86}Sr$ in the urine or blood of said subject on a daily or weekly basis. Where the dosage being administered shows efficacy in that the urine or blood of the subject shows an increase in the heavier calcium isotope, the dosage can be maintained. If the dosage of the therapeutic agent does not produce a desired increase in the heavy calcium isotope in the urine or blood of the subject, or indeed produces an increase in the lighter isotope in the urine of the subject, the therapy can be quickly and suitably modified to produce a greater effect.

While PTH is discussed above, the methods of the present invention can be used to determine the efficacy of any bone enhancing agents known in the art to increase bone formation, bone density or bone mineralization, or to prevent bone resorption. Such bone enhancing agents include, for example, natural or synthetic hormones, such as selective estrogen receptor modulators (SERMs), estrogens, androgens, calcitonin, prostaglandins and parathormone; growth factors, such as platelet-derived growth factor, insulin-like growth factor, transforming growth factor, epidermal growth factor, connective tissue growth factor and fibroblast growth factor; vitamins, particularly vitamin D; minerals, such as calcium, aluminum, strontium, lanthanides (such as lanthanum (III) compounds as described and used in U.S. Pat. No. 7,078,059, incorporated herein by reference) and fluoride; isoflavones, such as ipriflavone; statin drugs, including pravastatin, fluvastatin, simvastatin, lovastatin and atorvastatin; agonsists or antagonist of receptors on the surface of osteoblasts and osteoclasts, including parathormone receptors, estrogen receptors and prostaglandin receptors; bisphosphonate and anabolic bone agents. In one embodiment, vitamin D, calcium, or both are concurrently administered with the pharmaceutical formulations of the present invention.

Where $^{44}Ca/^{42}Ca$ and/or $^{87}Sr/^{86}Sr$ are administered to the subject they are advantageously formulated as dietary supplements and may be in the form of pill, powders, liquids and the like that can be taken orally. In some embodiments, the $^{44}Ca/^{42}Ca$ and/or $^{87}Sr/^{86}Sr$ also may be administered as part of the pharmaceutical compositions and formulations that are being used to enhance bone density and formation.

The present invention also encompasses a kit including the $^{44}Ca/^{42}Ca$ and/or $^{87}Sr/^{86}Sr$ containing compositions and to be used with the methods of the present invention. The kit can contain a vial, for example, which contains a formulation of $^{44}Ca/^{42}Ca$ and/or $^{87}Sr/^{86}Sr$, either dried or in liquid form. The kit further includes instructions in the form of a label on the vial and/or in the form of an insert included in a box in which the vial is packaged, for the use and administration of the compounds. The instructions can also be printed on the box in which the vial is packaged. The instructions contain information such as sufficient dosage and administration information so as to allow a worker in the field to administer the drug. It is anticipated that a worker in the field encompasses any doctor, nurse, or technician who might administer the drug, or a patient who might self-administer the $^{44}Ca/^{42}Ca$ and/or $^{87}Sr/^{86}Sr$ composition and monitor its presence in the blood or urine of patient. The kits of the invention therefore also may include the appropriate instruments and receptacles to allow a sample of blood or urine to be taken from the subject and analyzed for the presence of $^{44}Ca/^{42}Ca$ and/or $^{87}Sr/^{86}Sr$.

Examples

The procedure we use to measure Ca isotope ratios in human samples is as follows:

Sample material (blood, urine, etc.) is collected and stored in containers cleaned of any contaminating Ca. No preservatives or other materials are added to the samples unless previous analysis has shown these materials to have a Ca concentration less than $1/5000^{th}$ that of the biological material to be analyzed. Sufficient sample is collected to supply 20 micrograms (ug) of Ca, which is enough for 8-10 replicate isotopic analyses. This much Ca is reliably present in 0.45 ml of whole blood and 1.0 ml of urine. Samples are stored frozen.

Samples are thawed immediately before preparation. 0.5 ml of 16N HNO3 is added. Samples are shaken vigorously, held at room temperature for one hour, shaken vigorously again, and quantitatively transferred to acid-washed centrifuge tubes. Samples are centrifuged to remove insoluble debris, such as cell fragments and dust. Cleaned samples are transferred to 1.5 ml microcentrifuge tubes and processed.

We now are employing a novel modification of this protocol in which Ca samples are loaded in HBr rather than HCl. This modification dramatically improves the ability of column chemistry to separate Ca from other elements, such as Ti, an improvement over previous techniques that is essential for eventual automation of the sample preparation process.

In the HBr process resin is loaded into 250 mL glass columns and cleaned with:

5 column volumes of 18 MOhm water
5 column volumes of reagent grade 12M HCl
3 column volumes of 18 MOhm water
2.5 column volumes of 100% ethanol
2 column volumes of 18 MOhm water
8 column volumes of 2.5M HCl In the HBr process resin is loaded into 250 mL glass columns and cleaned with:

Each step is added in increments of one column-volume. The resin is then conditioned in 5 ml of 8.8 M HBr. The sample is dissolved in 1 ml 8.8 M HBr. The sample is loaded, and the Ca sticks to the resin while the matrix is eluted. The matrix elution volume is 12-15 ml. The column is then converted to a HF matrix with 5 ml of 0.1 M HF and Ti is eluted with 0.1 M HF (12 ml). The Ca and Sr are eluted in 30 ml 6 M HCl. The elution is dried down and the Sr column is then run, following the HCl protocol After column chemistry, samples are diluted to 5 ppm Ca in 0.32M HNO3 and analyzed on a Neptune multi-collector inductively coupled plasma mass spectrometer (MC-ICP-MS) with the cup configuration: $^{42}$Ca (L4), $^{43}$Ca (L2), $^{44}$Ca (L1), $^{46}$Ca (H1), $^{47}$Ti (H2) and $^{48}$Ca (H3). Typically, a 5 ppm solution provides about 4 V on $^{44}$Ca in medium resolution at ~1200 W. Data are collected in 30 cycles of 4.2 seconds, with a 60 second uptake time and 75 second washout time using a 50 microliter per minute nebulizer. We typically run using the sample-standard bracketing method, with ICP-1 as our bracketing standard. This is an ICP standard solution, Lot #X106396A. We throw out the $^{46}$Ca data due to low abundance. We sit on the shoulder of the isotope peak to avoid prominent interferences including $^{40}$ArH$_2^+$ and $^{14}$N$_3^+$ on $^{42}$Ca, $^{14}$N$_3$H$^+$ on $^{43}$Ca, $^{12}$C$^{16}$O$_2^+$ and $^{14}$N$_2$$^{16}$O$^+$ and on $^{44}$Ca and monitor $^{47}$Ti to assess the potential $^{48}$Ti interference on $^{48}$Ca. We are not currently making a correction on $^{48}$Ca for Ti, since the data are often considerably worse if we do so (presumably, there is some other interference at mass 47 in addition to $^{47}$Ti. We can not resolve Sr$^{++}$ on $^{43}$Ca or $^{44}$Ca instrumentally ($^{84}$Sr is very small in abundance relative to other Sr isotopes and so cannot easily be monitored), so we require that our samples have Ca/Sr>10,000 prior to MC-ICP-MS analysis. Theoretically, we should be able to resolve $^{41}$KH$^+$, but have not clearly observed this, so that high K samples are also a problem; we require that samples have K/Ca of <0.5.

Figure 1:
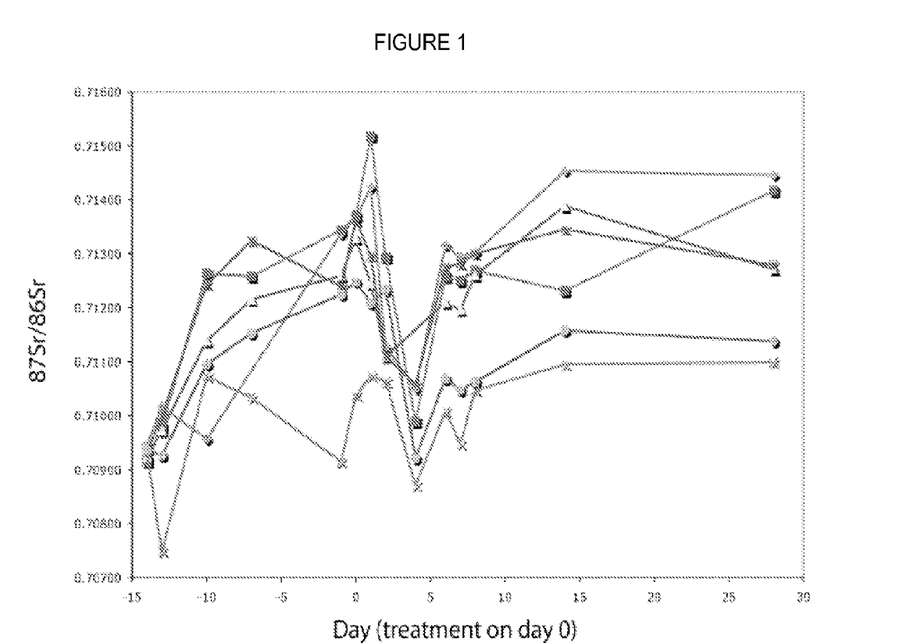
FIG. 1: Urinary 87Sr/86Sr of six female rhesus monkeys raised on a diet with an 87Sr/86Sr of ca 0.70900 switched on day −14 to a dietary 87Sr/86Sr of ca 0.71600.
Figure 2:
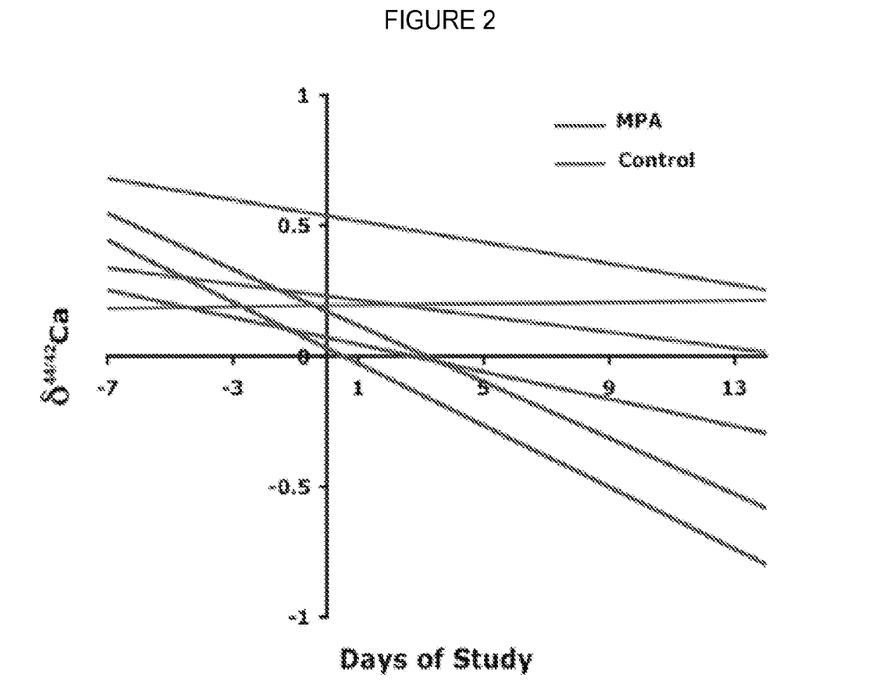
FIG. 2: Average slope of change in urinary d44Ca in female rhesus monkeys given an estrogen suppressing drug (MPA) or a saline injection (Control) on day 0.
Figure 3:
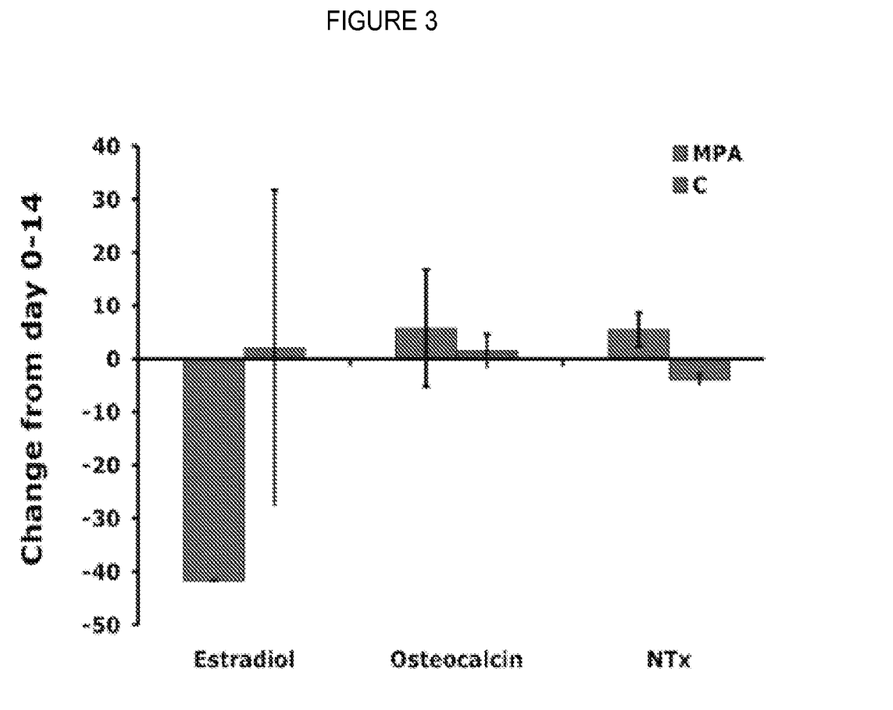
FIG. 3: Change in circulating levels of estrodiol, osteocalcin (a biochemical marker of bone formation) and NTx (a biochemical marker of bone resorption) between days 0 and 14 of the same study as FIG. 2.

The results from these studies are shown in FIGS. 1-3. FIG. 1 shows the urinary 87Sr/86Sr of six female rhesus monkeys raised on a diet with an 87Sr/86Sr of ca 0.70900 switched on day −14 to a dietary 87Sr/86Sr of ca 0.71600, resulting in an isotopic offset between dietary and bone Sr. The sharp drop in 87Sr around day 1 is interpreted as rapid bone loss in response to anesthesia.

FIG. 2 shows the average slope of change in urinary d44Ca in female rhesus monkeys given an estrogen suppressing drug (MPA) or a saline injection (Control) on day 0. Estrogen suppression is known to cause bone loss. d44Ca of the MPA group is significantly lower than that of control by day 5, demonstrating the ability of Ca isotopic analysis detect changes in bone mineral balance within days of onset.

FIG. 3 shows the change in circulating levels of estrodiol, osteocalcin (a biochemical marker of bone formation) and NTx (a biochemical marker of bone resorption) between days 0 and 14 of the same study as FIG. 2. Although the NTx data hint at the expected increase in bone resorption in the MPA group, the change was not significantly significant. Long-term studies using the same animal model reveal a significant drop in bone mineral density in response to estrogen suppression after six months.

Example

In the present Example, the goal of the research was to test the hypothesis that rapid changes in bone mineral balance (BMB) can be detected using Ca isotopes, utilizing measurements of natural, biologically induced variations in the abundances of the Ca isotopes in urine. Data confirming this hypothesis (FIGS. 4 and 5) have been produced. These results indicate that Ca isotopes can serve as an "inorganic biomarker" that provides significant information about changes in BMB after just 7 days of bed rest, long before detectible changes in bone mineral density. The ability to rapidly assess changes in BMB that the present invention provides should permit rapid evaluation of countermeasures to bone loss, accelerate the pace of discovery of new treatments for metabolic bone disease, and provide novel insights into the dynamics of bone metabolism.

Ca isotope variations are a result of the six naturally occurring Ca isotopes ($^{40}$Ca, $^{42}$Ca, $^{43}$Ca, $^{44}$Ca, $^{46}$Ca and $^{48}$Ca) reacting at different rates depending on mass. In soft tissue, these variations exist because bone formation depletes soft tissue of light Ca isotopes. Bone resorption releases that isotopically light Ca back into soft tissue. As a result, the Ca isotope composition of soft tissue should shift toward lighter values when bone is resorbed, and toward heavier values when bone is formed. As a consequence, Ca isotopes provide a direct and quantitative measure of net bone mineral balance.

In an earlier study, we observed variations in Ca isotope abundances consistent with net bone resorption after 4 weeks in a 90-day bed rest study (data collected at 0, 4, 8 and 12 weeks) (Skulan et al., Clin. Chem., 53: 1155, 2007). These variations correlated with bone density measurements. To assess the rapidity with which this signal appears, our NASA HRP-funded effort centers on a new 30-day bed rest study involving 12 patients on controlled diet, monitored for 12 days prior to bed rest and 7 days post bed rest. Samples of urine were collected frequently throughout the study to examine short-term variations.

To test the hypothesis it was necessary to design new procedures and protocols for sample preparation and instrumental analysis because the required sensitivity and sample throughput dictated that we use multiple collector inductively couple plasma mass spectrometry (MC-ICP-MS) rather than thermal ionization mass spectrometry (TIMS). Critical issues that needed to be resolved included devising a new ion exchange separation procedure to adequately extract and purify Ca from complex biological samples. The new technique is both sensitive and precise; the abundance ratio of $^{44}$Ca/$^{42}$Ca can be measured using <25 µg of Ca with a typical precision of ±0.15(±2σ) parts per thousand (per mil; ‰).

Figure 4:
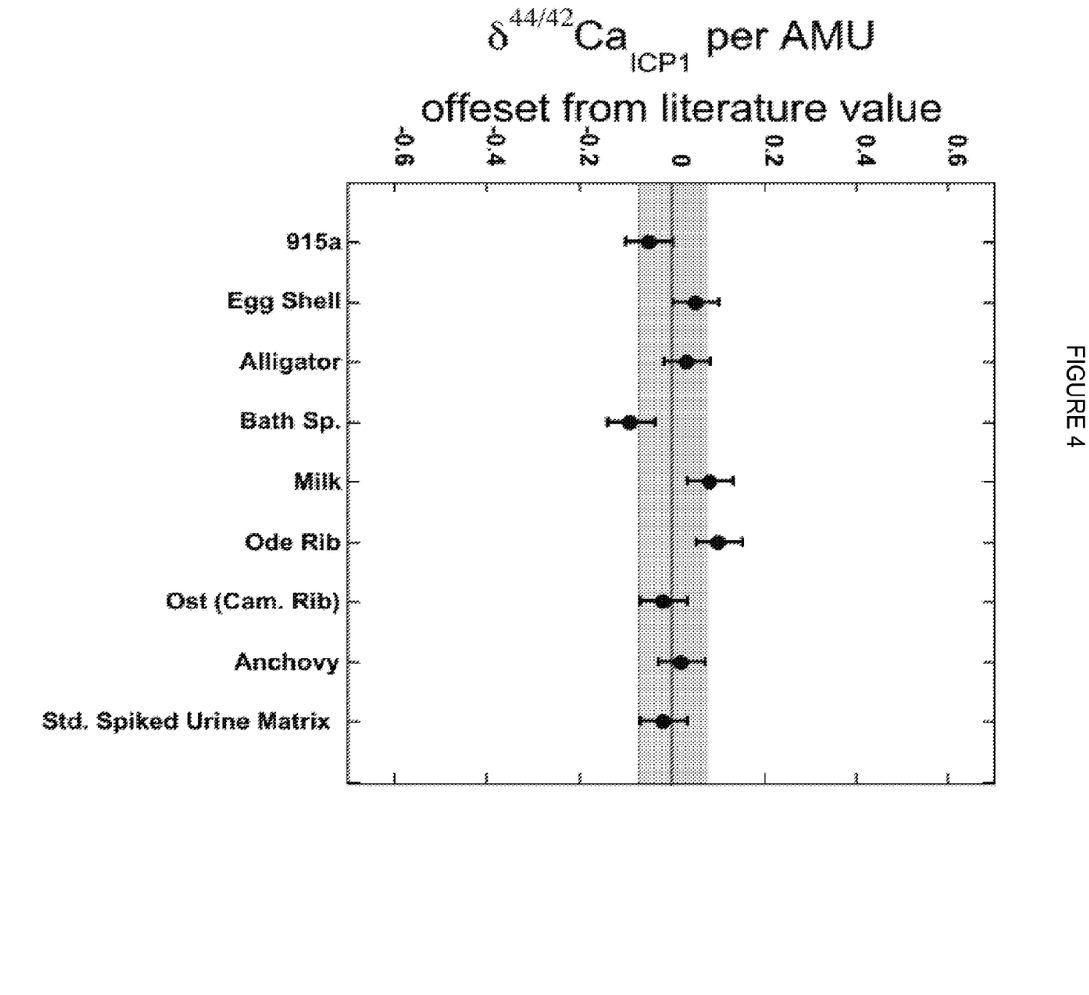
FIG. 4: Comparison of Ca isotope compositions determined by MC-ICP-MS (this study) and TIMS (literature values). Comparisons are simple differences of $\delta^{44/42}Ca$ determinations by the two methods ($\delta^{44/42}Ca$ is defined below). All samples were purified using our new protocols. No urine sample was available that was previously measured by TIMS. Therefore, the sample "std. spiked urine matrix" is a urine sample from which we removed Ca, after which we added Ca of known isotopic composition. The sample was then processed identically to others. Data are reported as $\delta^{44/42}Ca$ per AMU=$[^{44}Ca/^{42}Ca_{sample}/^{44}Ca/^{42}Ca_{std}-1]\times 1000$‰2 AMU.

Measurements are also accurate, based on comparison with published Ca isotope data obtained by TIMS (FIG. 4).

Ca Isotopes and BMB.

Figure 5:
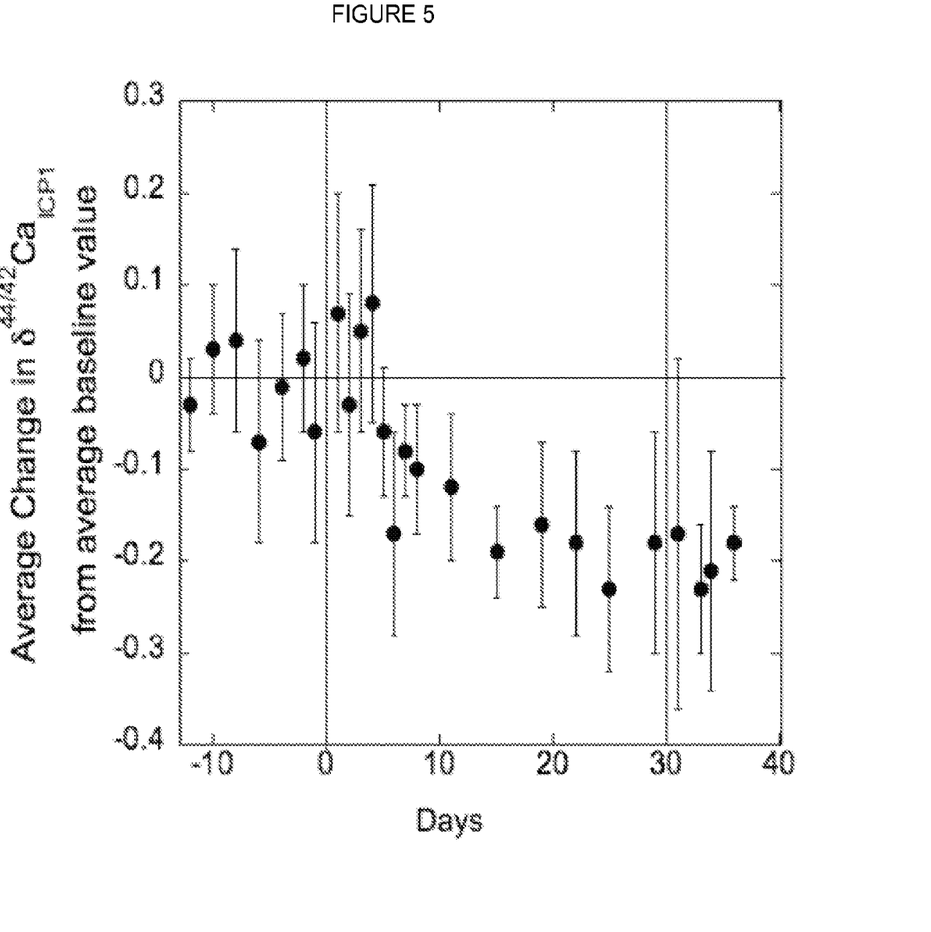
FIG. 5: Ca isotope variations in bed rest urine samples. Variations were determined individually for each patient by calculating the difference between the value at each time point and the average of the pre-bed rest values for that patient. This difference determination was necessary because initial $\delta^{44/42}Ca$ varied among patients. Decrease in $\delta^{44/42}Ca$ on about day 7 of bed rest reflects the onset of negative bone mineral balance. For ease of presentation, the determinations from the 12 patients are averaged such that the values reported at each time point represent the mean (±2se) of all difference determinations from that time. Most points represent the mean of at least 6 determinations; analyses of remaining urine samples are in progress.

After 7 days of bed rest, the mean value of $^{44}Ca/^{42}Ca$ decreases by approximately 0.3‰ for all 12 patients (FIG. 5). This decrease is most simply explained as reflecting the onset of negative BMB. $^{44}Ca/^{42}Ca$ remains low during the remainder of bed rest and into the post bed rest period. Pre bed rest $^{44}Ca/^{42}Ca$ of individual patients varied by ca 0.14%, possibly reflecting dietary variations in Ca isotopes. For the 12 days pre bed rest the average $^{44}Ca/^{42}Ca$ remained, high with no systematic change in the average of all patients.

There is an ongoing study from which samples from the 30-day study will be analyzed. In addition to the remaining urine samples, the inventors are investigating the Ca isotope compositions of diet to determine the extent to which dietary variations affect Ca isotope abundances in soft tissue. Blood samples are also being investigated, as a comparison of blood and urine will provide insights into the magnitude of isotope fractionation in the kidneys and the relative utility of these sample types.

The invention claimed is:

1. A method of measuring changes in bone mineral balance in a subject in response to a therapy or other intervention comprising:
   a. determining a baseline ratio of two calcium isotopes in a first sample of said subject;
   b. administering to said subject the therapy;
   c. mixing a second sample from said subject with HBr to form a mixture, wherein the second sample and HBr mixture is loaded on a column resin and processed such that purified calcium is eluted with HCl, and wherein said second sample is collected from said subject at an interval of about one hour to about five days after the administration of said therapy; and
   d. determining a mixture ratio of the two calcium isotopes purified from said second sample and HBr mixture, wherein a difference between the baseline ratio and the mixture ratio is indicative of an alteration in the bone mineral balance in said subject.

2. The method of claim 1, wherein an increase in said mixture ratio of the two calcium isotopes as compared to the baseline ratio is indicative that the subject has a rate of bone formation that exceeds bone dissolution.

3. The method of claim 1, wherein a decrease in said mixture ratio of the two calcium isotopes as compared to the baseline ratio is indicative that the subject has a rate of bone dissolution that exceeds bone formation.

4. The method of claim 1, wherein the two calcium isotopes are selected from the pairs $^{48}Ca/^{46}Ca$, $^{48}Ca/^{44}Ca$, $^{48}Ca/^{43}Ca$, $^{48}Ca/^{42}Ca$, $^{48}Ca/^{40}Ca$, $^{46}Ca/^{44}Ca$, $^{46}Ca/^{43}Ca$, $^{46}Ca/^{42}Ca$, $^{46}Ca/^{40}Ca$, $^{44}Ca/^{42}Ca$, $^{44}Ca/^{43}Ca$, $^{44}Ca/^{40}Ca$, $^{43}Ca/^{42}Ca$, $^{43}Ca/^{40}Ca$ and $^{42}Ca/^{40}Ca$.

5. The method of claim 1, wherein the calcium isotopes are $^{44}Ca/^{42}Ca$.

6. The method of claim 1, further comprising monitoring the ratio of calcium isotopes of the dietary calcium intake of said subject prior to determining the baseline ratio.

7. The method of claim 1 further comprising modifying the diet of said subject to perturb the natural calcium intake and replace it with a calcium dietary supplement comprising a known $^{44}Ca/^{42}Ca$ content.

8. The method of claim 1, further comprising determining the short-term change in levels of $^{44}Ca/^{42}Ca$ in response to bed rest in said subject.

9. The method of any of claims 1 though 8 wherein said sample is selected from the group consisting of blood, urine, hair, bone, muscle, skin, nails, saliva or any other tissue or biological material.

10. The method of claim 1 further comprising determining a ratio of two naturally occurring stable isotopes of strontium $^{87}Sr/^{86}Sr$ in the soft tissue of said subject wherein an increase in the heavier strontium isotope as compared to the lighter isotope is indicative of a higher rate of bone formation than bone dissolution and an increase in the lighter strontium isotope as compared to the heavier isotope is indicative of a higher rate of bone dissolution than bone formation.

11. The method of claim 10, further comprising determining a baseline ratio of $^{87}Sr/^{86}Sr$ in said subject.

12. The method of claim 10, further comprising administering to said subject a dietary supplement to elevate said ratio of $^{87}Sr/^{86}Sr$ in said subject to a level above that found in normal diet of said subject and allowing a sufficient period of time to elapse to allow dissemination and incorporation of said elevated ratio of $^{87}Sr/^{86}Sr$ into the bone mass of said subject prior to step (b).

13. A method of determining a change in the bone mineral balance in a subject comprising the steps of:
   a. collecting a sample selected from the group consisting of blood, urine, hair, feathers, horns, hooves, nails, skin, bone, shell or any other hard or soft tissue from the animal;
   b. mixing the sample with HBr to form a mixture, wherein the sample and HBr mixture is loaded on a column resin and processed such that purified calcium and strontium are eluted with HCl, and;
   c. measuring the relative amount of a first calcium isotope to a second calcium isotope purified from the mixture of said sample and HBr;
   d. measuring the relative amount of a first strontium isotope and a second strontium isotope purified from the mixture of said sample and HBr;
   e. comparing said measured relative amount of the calcium isotopes in the mixture and said relative amount of strontium isotopes in the mixture with a relative amount of said pairs of isotopes in a comparison specimen other than the sample; and
   f. determining from the comparison step whether there is an enhanced bone formation or an enhanced bone resorption in said subject wherein an increase in the heavy isotopes of calcium and strontium is indicative of an increase in bone formation and/or a decrease in bone resorption and an increase in the light isotopes is indicative of an increase in bone resorption and/or a decrease in bone formation.

14. The method of claim 13, wherein said measured relative amounts of calcium and strontium isotopes are measured using multiple collector inductively couple plasma mass spectrometry.

15. The method of claim 1, wherein said baseline ratio and said mixture ratio are measured using multiple collector inductively couple plasma mass spectrometry.

* * * * *